United States Patent [19]

Wands et al.

[11] Patent Number: 5,422,239

[45] Date of Patent: Jun. 6, 1995

[54] IMMUNOASSAY UTILIZING MONOCLONAL HIGH AFFINITY IGM ANTIBODIES

[75] Inventors: Jack R. Wands, Waban, Mass.; Vincent R. Zurawski, Jr., West Chester, Pa.

[73] Assignee: General Hospital Corporation, Boston, Mass.

[21] Appl. No.: 51,176

[22] Filed: May 15, 1987

Related U.S. Application Data

[60] Continuation of Ser. No. 587,465, Mar. 8, 1984, abandoned, which is a division of Ser. No. 188,735, Sep. 19, 1980, Pat. No. 4,879,219.

[51] Int. Cl.[6] .............. G01N 33/543; G01N 33/569; G01N 33/577
[52] U.S. Cl. .................... 435/5; 435/7.94; 435/70.21; 435/172.2; 435/240.27; 436/513; 436/518; 436/531; 436/532; 436/533; 436/538; 436/540; 436/541; 436/542; 436/548; 436/820; 530/388.3
[58] Field of Search ............... 435/4, 5, 7, 68, 70, 435/172.2, 240.27, 188, 235, 236; 935/89, 102–104, 106, 108, 110; 424/86, 89; 530/387, 808; 436/513, 531, 532, 533, 538, 540, 541, 542, 548, 518, 820

[56] References Cited

U.S. PATENT DOCUMENTS

| | | | |
|---|---|---|---|
| 4,098,876 | 7/1978 | Piasio et al. | 424/1.1 |
| 4,244,940 | 1/1981 | Jeong et al. | 424/1.1 |
| 4,248,965 | 2/1981 | Mochida et al. | 435/7 |
| 4,271,145 | 6/1981 | Wands et al. | 424/85 |
| 4,361,647 | 11/1982 | Remington et al. | 435/7.22 |
| 4,376,110 | 3/1983 | David et al. | 436/513 |
| 4,491,632 | 1/1985 | Wands et al. | 435/240.27 |
| 4,837,167 | 6/1989 | Schoemaker et al. | 436/513 |

FOREIGN PATENT DOCUMENTS

| | | |
|---|---|---|
| 0038642 | 10/1981 | European Pat. Off. . |
| 0042755 | 12/1981 | European Pat. Off. . |
| 0044219 | 1/1982 | European Pat. Off. . |
| 0045103 | 3/1982 | European Pat. Off. . |
| 0048357 | 3/1982 | European Pat. Off. . |
| 0071635 | 4/1986 | European Pat. Off. . |
| 0059754 | 6/1986 | European Pat. Off. . |
| 2481318 | 4/1981 | France . |
| 2029571 | 3/1980 | United Kingdom . |
| 2074727 | 4/1981 | United Kingdom . |

OTHER PUBLICATIONS

Steensgaard, J. et al, Molecular Immunology, vol. 17; pp. 1315–1318 (1980).

Shih, J. W. et al, Journal of Immunology, vol. 120 (2), pp. 520–525 (1978). Antigenicity of Major Polypeptides of HBsAg.

Frankel, M. E. et al, Molecular Immunology, 16: 101–106 (1979).

Koprowski, H. et al, Proc. Natl. Acad. Sci, USA 74(7): 2985–2988 (Jul. 1977).

Dreesman et al., "Biophysical and Biochemical Heterogeneity of Purified Hepatitis B Antigen," *Journal on Virology*, V. 10, No. 3 (Sep. 1972) pp. 469–476.

Robinson, "The Genome of Hepatitis B Virus," *Annual Review Microbial*, V. 31, (1977) pp. 357–377.

Peterson et al., Partial Amino Acid Sequence of Two Major Component Polypeptides of Hepatitis B Surface Antigen, *Proc. National Academy of Science USA*, V. 74, No. 4 (Apr. 1977) pp. 1530–1534.

Appendix, *Monoclonal Antibodies. Hybridomas, a New Dimension in Biological Analyses*, Edited by Roger H. Kennet et al, Published Jul. 1980 by Penum Press., pp. 363–419.

(List continued on next page.)

*Primary Examiner*—David Saunders
*Attorney, Agent, or Firm*—Sterne, Kessler, Goldstein & Fox

[57] ABSTRACT

Hybridomally produced monoclonal IgM antibodies. having high affinity are useful for the immunoassay and purification of vital antigens.

8 Claims, 2 Drawing Sheets

OTHER PUBLICATIONS

Zurawski, Jr., et al, an *Abstract Reproduction* of paper presented at 52nd Scientific Sessions of American Heart Association, Nov. 12–15, 1979, California.

Buschagger, F. et al, "Protides Biol. Fluids,", 1980, 28th, pp. 511–515 (Also found in *Chemical Abstracts* 94:203339f).

Opposition to European Patent Appln. 82900761-6 (1987).

Immunochemistry, 1972, vol. 9, pp. 325–340, C. L. Hornick et al.

Molecular Immunology, vol. 17, pp. 791–794, M. Votila et al.

Proc. Natl. Acad. Sci. USA vol. 76, No. 7, pp. 3532–3536, A. C. Cuello et al.

Immunochemistry, 1972, vol. 9, pp. 325–340, C. L. Hornick et al.

Immunogenetics 9:137–147 1979, B. M. Longenecker et al.

"Principles of Radioimmunoassay", Thomas J. Gil, II, pp. 169–171 Manual of Clinical Immunology, 1976.

Opposition to European Patent Appln. 81902711.1-2107 (1987).

IMMUNOASSAY UTILIZING MONOCLONAL HIGH AFFINITY IGM ANTIBODIES

This application is a continuation of application Ser. No. 587,465 filed Mar. 8, 1984 now abandoned, which is a division of application Ser. No. 188,735, filed Sep. 19, 1980 and now U.S. Pat. No. 4,879,219.

BACKGROUND OF THE INVENTION

1. Field of the Invention

The present invention relates to an immunoassay system which utilizes hybridomally produced high affinity IgM antibodies.

2. Description of the Prior Art

The use of immunoassay for the detection of minute amounts of substances in physiological fluids is very well known in the art. The assay basically depends on the binding interaction between an antigen and an antibody therefor. In the great majority of systems described in the prior art, the antibody is usually immunoglobulin G (IgG). Among these, the polyclonal IgG's have until recently been routinely utilized (see for example T. Chard, "An Introduction to Radioimmunoassay and Related Techniques" North-Holland Publishing Company, 1978).

The advent of hybridomal techniques has brought about the possibility of producing homogeneous populations of highly specific antibodies against a variety of antigens. Thus, Koprowski et al U.S. Pat. No. 4,172,124 describe antibodies demonstrating specificities for malignant tumors produced by somatic cell hybrids between myeloma cells and spleen or lymph cells. Koprowski et al U.S. Pat. No. 4,196,265 describe continuous cell lines of genetically stable fused cell hybrids capable of producing large amounts of IgG antibodies against specific viruses, such as influenza virus, rabies, mumps, SV40, and the like. Zurawski et al, Federation Proceedings 39:4922 (1980), disclose hybridomas producing monoclonal IgG antibodies against tetanus toxin. Frankel and Gerhard, Molecular Immunology, 16:101–106 (1979) also disclose monoclonal antiviral hybridoma IgG antibodies described as "true bivalent antibodies" Frankel and Gerhard, at 105. The Frankel and Gerhard paper describes what are probably the prior art antibodies having the highest affinities to date. The monoclonal antibodies of Frankel and Gerhard have K values (binding constants determined from Scatchard plots) in the ranges of from less than $10^5 M^{-1}$ to about $10^{10} M^{-1}$. The aforementioned Zurawski et al paper describes monoclonal antibodies having K association constants in the range of $3.5–5.4 \times 10^8 M^{-1}$.

The use of IgM antibodies has received relatively less attention in the immunoassay art. IgM antibodies consist of 5 units each the approximate size of IgG joined by a so-called J (joining) chain. The IgM molecule has a valency of 10, although quantitative antigen binding measurements often detect only 5. IgM's are extremely sensitive to reducing agents, they self-aggregate readily and precipitate out of solution, and have been found to bind in a non-specific manner. These reasons, among others, have heretofore prevented their extensive use. Because of the polyvalency of IgM antibodies, various suggestions have been made in the art concerning the theoretical binding affinity of these antibodies towards antigens. For example Metzget, has suggested that it would be "intuitively obvious" that an antibody with multiple binding sites would bind more firmly than a univalent or bivalent antibody to a multivalent antigen. Metzger however qualifies this statement recognizing that the energetics of binding would be highly dependent on the number and topology of antigenic determinants, the distribution of combining sites in space and the balance between the free energy of binding released by combining site/determinant interactions and high free energy required to maximize the number of multiple flexible conformations existing in such large molecules. These qualifications are even more stringent when it comes to cross linking of translationally independent determinants such as in agglutination. Mathematical models have been developed describing the theoretical binding of multivalent IgM antibodies to multideterminant antigen particles (Crothers and Metzger, Immunochemistry, Volume 9, 341357 (1972)). It has even been suggested (Ehrlich, journal of Theoretical Biology, 81:123–127 (1979)) that multivalency might theoretically increase specificity. All of these expectations of the art, as represented by the intuitive feelings and purely theoretical mathematical models, have been at odds with the experimental facts except in certain specific instances, infra. Although IgM antibodies are multivalent, the binding affinities observed for them have, prior to this invention, always been substantially less than the binding affinities for IgG antibodies. It is for this reason that IgM's have not routinely been utilized for immunoassays, other than in certain specific circumstances, infra. The art has explained the observed poor binding affinity of IgM antibodies, as being due to the structural features of the molecules, and the probability that combining sites of IgM molecules have lower avidity for antigens than do those of IgG's. Cunningham, A. ("Understanding Immunology", Academic Press Inc., 1978, at 33), in suggesting why quantitative antigen binding measurements with larger antigens on IgM antibodies detect only 5 and not 10 binding sites, discusses the possibility that for reasons of steric restriction, all the sites cannot attach to the same antigenic structure at the same time.

Faced with the lesser utility of IgM antibodies in conventional precipitation or immunoassay techniques, the prior art nevertheless details some special circumstances under which this class of antibodies can, and has been used. Soothill et al U.S. Pat. No. 4,210,622 describe the use of heterologous low affinity IgM obtained from myeloma serum for the selective determination of immune complexes. This technique takes advantage of the fact that low affinity IgM's will selectively bind antibody-antigen complexes even in the presence of individual components of the complex. Soothill et al U.S. Pat. No. 4,141,965 describe a method wherein low affinity heterologous IgM antibodies are used to agglutinate antigen-coated latex particles. When physiological fluid containing antigen is added to the agglutinate mixture, an inhibition-of-agglutination occurs. Gopalakrishnan and Karush, Journal of Immunology, 113: 769–778 (1974), disclose the use of IgM antibodies of restricted heterogeneity induced by a lactoside determinant, for the binding of conjugates of the lactoside determinant with bacteriophage $\phi$X174. These authors report that the constant for the binding of the antibody to the conjugate ($\sim 10^9 M^{-1}$) is greater by a factor of 10,000 than that for the lactoside itself ($\sim 10^5 M^{-1}$). Blank et al, Journal of Immunology, 108:665–673 (1972)) disclose affinity constants for grouper IgM's in the order of $10^4 M^{-1}$. A specific instance of an IgM antibody, rheumatoid factor (RF) has also been utilized for immunoassays in the past. RF's are IgM antibodies directed towards antigenic determinants present on autologous immunoglobulin. Lurhuma et al, Clinical and Experimental Immunology, 25:212-226 (1976), describe the use of RF as an agglutinant for IgG coated particles, and an inhibition of agglutination effect which occurs in the presence of antibody-antigen complexes. Masson et al U.S. Pat. No. 4,062,935 describe a similar system to that of Lurhuma.

Monoclonal RF to human IgG has been used by Eisenberg, Immunochemistry, 13:355-359 (1976) to demonstrate binding to aggregated IgG. The binding of monoclonal RF to aggregated IgG is increased by a factor of greater than $10^6$ (as determined by radioimmunoassay) over the binding of RF to nonaggregated, monomeric, IgG.

In sum, the use of IgM antibodies, whether polyclonal or monoclonal has been restricted to assaying for antibody-antigen complexes, aggregated IgG's, or, by an inhibition of agglutination technique, to antigen-coated latex particles. Because of the poor binding affinity of IgM's as well as their self-aggregating tendency, non-specific interactions and sensitivity to reducing agents, it has generally been assumed in the art that IgM antibodies were not useful for highly sensitive immunoassay techniques.

SUMMARY OF THE INVENTION

It is an object of the invention to provide a highly sensitive immunoassay system for vital antigens.

Another object of the invention is to provide an immunoassay system utilizing IgM antibodies.

These and other objects of the invention as will hereinafter become more readily apparent have been attained by providing:

An immunoassay system utilizing an antibody to assay for a vital antigen, wherein said antibody is a hybridomally produced monoclonal high affinity IgM.

Another object of the invention is to provide solid phase bound hybridomally produced IgM antibodies useful for immunoassay techniques and for purification methods.

Yet another object of the invention is to provide a purification method for vital antigens which utilizes solid phase bound hybridomally produced IgM antibodies.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 3 and 4 represent affinity columns prepared with 28 and 65 mg of ascites fluid protein from clones 5D3 and 2F11. It should be noted that the monoclonal hybridomally produced IgM anti-HBs coupled to Sepharose 6B bound HBsAg, and substantial antigenic activity and protein were recovered following elution with glycine-HCl pH2.6. Negative serum controls for HBsAg activity where 426 106 cpm and positive serum controls were 12,462±321 cpm.

DESCRIPTION OF THE PREFERRED EMBODIMENTS

Wands and Zurawski, copending U.S. patent application Ser. No. 086,947 filed Oct. 22, 1979 at the U.S. Patent Office, now U.S. Pat. No. 4,271,145 and which is in its entirety herein incorporated by reference, discloses a process for hybridomally producing monoclonal IgM antibodies against a variety of antigens, especially vital antigens. The present invention arose out of the suprising discovery that the thus produced monoclonal IgM antibodies, not only show the homogeneous population specificity which is expected in hybridomally produced antibodies but, in addition, show unexpectedly high binding affinity constants for vital antigens. Although the art had intuitively predicted and theoretically modeled the possibility that IgM antibodies might show increased binding affinities, most experimental results obtained prior to this invention, as discussed previously, did not bear out these predictions, and even if they did to some extent, were not sufficiently useful for sensitive immunoassay techniques. The actually observed binding constants for polyclonal IgM antibodies have generally been in the range of $10^4-10^6 M^{-1}$. It was assumed prior to this invention that a certain variation in affinity constants existed in any population of IgM antibodies. It was not known however how high the affinity constants could be, and none had been observed to be higher than about $10^9 M^{-1}$. The present inventors have discovered that hybridomally produced antibodies against vital antigens can have affinity binding constants higher than $10^9 M^{-1}$ and as high as $10^{11} M^{-1}$.

Through the use of monoclonal hybridomally produced IgM antibodies, the present inventors have now simultaneously improved the specificity and the affinity of immunoassays, in all reactions between IgM antibodies and viral antigens. By increasing the affinity binding constant to the high values observed in the present invention, it is possible for the first time to carry out highly sensitive immunoassay procedures using IgM antibodies. The combined use of a hybridomally produced IgM antibody and a viral antigen allows the improvement in performance.

The specificity relates to the lack of cross reactivity or lack of interference in the antigen-antibody reaction by other substances present in the reaction mixture. Hybridomally produced antibodies in general, including IgG's, exhibit an extraordinary specificity since they are directed against a single determinant. However because they are directed against a single determinant, they bind to fewer sites on an antigen than classically (polyclonally) produced antibodies. This fact had been reflected in an existing fear in the prior art that the extraordinary specificity of monoclonally produced antibodies, would be a detriment to their utilization in sensitive clinically useful immunoassays. The present inventors however have now demonstrated that hybridomally produced IgM's can detect less antigen than the conventionally produced antibodies, despite their extraordinary specificity.

The hybridomally produced IgM antibodies for specific vital antigens utilized in the present invention can be obtained, for example, through the use of cell fusion techniques first described by Kohler and Milsrein (Nature, 255:495 (1975)). Lymphocytes from an animal immunized with the antigen of choice are fused to a continuously proliferating myeloma cell. Subsequently, hybrid cells are selected in hypoxanthine-aminopterin-thymidine (HAT) medium (Littlefield, Science, 145:709 (1964)). Those which produce the IgM antibody of choice are cloned and propagated indefinitely in tissue culture or in syngeneic or immunocompromised animals, or in athymic animals, for example nude mice. Such clones, are the progeny of single cell produced or monodisperse IgM antibodies, i.e., monoclonal IgM antibodies, which is directed to an individual determinant or an antigen. This determinant is expressed more than once on the surface of each individual viral particle or fragment thereof. Further details on the preparation of monoclonal IgM antibodies can be found in the aforementioned Wands and Zurawski U.S Pat. No. 4,291,145.

Other techniques of production might of course also be used, such as vital transformation, recombinant DNA and other gene splicing or manipulation techniques.

The hybridomally produced high affinity IgM antibodies of the present invention are those having affinity binding constants greater than $10^9 M^{-1}$, preferably greater than $10^{10} M^{-1}$, most preferably greater than $10^{11} M^{-1}$. In order to produce such high binding antibodies it is necessary to use a vital antigen or a fragment thereof.

Among the vital antigens which may be determined in the present invention are virus particles, fragments of virus particles such as whole coats, or individual molecular components of the coat, e.g., polypeptides or lipid or carbohydrate complexes. Examples of viral antigens are hepatitis B surface antigens, hepatitis Be antigen, hepatitis B core antigens, hepatitis A virus and isolated antigens thereof herpes viruses I and II, herpes virus Zoster, cytomegalovirus, Epstein-Barr virus, papova viruses such as BK or JC virus, measles virus, rubella virus, influenza or para influenza virus, or any other viruses known or suspected of being etiologic in pathogenesis or animals or plants.

The high affinity hybridomally produced IgM antibodies of the present invention can be used in any of the array of available immunoassay techniques which utilize the binding interaction between an antibody and an antigen, and the present invention is not limited to any of these techniques. The most common of these is radioimmunoassay (RIA). RIA is a well known technique and will not be described in detail here. For particulars, reference is made to Chard, "An Introduction to Radioimmunoassay and Related Techniques", North-Holland Publishing Company, 1978. Any of the many variations of RIA can be used, such as homogeneous phase RIA, or heterogeneous or solid phase RIA, single antibody methods or "double" antibody methods, and direct (forward) or reverse sandwich assays. Particularly preferred are solid phase systems wherein the antibody (IgG or IgM) is covalently coupled to an insoluble support so that both the antibody and the bound complex after incubation can be readily separated from the soluble free fraction. A wide variety of solid phase supports have been described, which include particles of dextran, cellulose, continuous surfaces such as polystyrene or polypropylene discs, walls of plastic tubes, glass discs, glass particles, and the like.

Particulate solid phases are widely used for a variety of different assays and are included in the present invention. Antibodies are attached to the particles by any of a number of techniques designed to yield a non-reversible covalent or non-covalent link between protein and particle, for example directly or by cyanogen bromide activation. Other alternatives are the use of antibodies entrapped in the interstices of a polyacrylamide gel, or bound to magnetic particles. The assay tube is set up with sample or standard, tracer and the appropriate amount of solid phase bound antibody, plus a detergent to prevent aggregation of the particles and non-specific absorption of the tracer. After an incubation period during which the tubes are continuously mixed, the solid phase is sedimented by centrifugation; the supernatant is removed and the solid phase subject to two or more washes with buffer in order to remove free tracer trapped within and between the particles. The counts on the solid phase (bound fraction) are then measured. Immunoradiometric assays, Chards, supra at 423, can also be used. When a second antibody radioimmunoassay system is used, the second antibody may be IgM or may be IgG.

Another immunoassay technique useful with the IgM antibodies of the present invention is enzyme immunoassay. This technique is also well known to the art and reference is made to Schuurs and VanWeemen, Clinica Chimica Acta, 81:1–40 (1977). In this technique, enzymes are applied as labels on antigen or antibodies for identification and localization of the immunoreactants. Any method in which the extent of binding of enzyme-labeled antigen, or enzyme labeled-antibody to its immunoreactant is measured, is included in this invention. Enzyme immunoassays can be classified as homogeneous or heterogeneous, depending on whether the labeled reagent behaves differently or identically whether or not it is bound to specific counterparts in the immunoreaction, and which therefore may or may not require physical separation of the reactants into two fractions. The variety of enzymes used, methods of linking enzymes to the immunological components, purification of the conjugates, as well as various assay principles and methods are well described in the aforementioned Schuurs and VanWeemen article. Needless to say, any enzyme immunoassay which has used IgG antibodies in the past can be used with the high affinity IgM antibodies of the present invention.

Another immunoassay method useful in the present invention is the latex agglutination method. In this method, latex particles are coated with vital antigen and incubated with high affinity hybridomally produced IgM antibodies. Inhibition of agglutination will occur when a sample of physiological fluid containing the vital antigen is incubated with this mixture. The inhibition of agglutination can either be followed with a counter or by recently developed infrared absorption techniques. An alternative is to coat the latex particles with the hybridomally produced IgM antibodies. Incubation of these coated particles with physiological fluid comprising vital antigen will cause agglutination. Instead of latex particles, animal cells such as red blood cells can of course be used. In this case, the technique becomes a variation of the well known hemagglutination technique used with antibodies and red blood cells.

Other useful immunoassay techniques are those using other labeling techniques such as:

fluorescent dyes (Aalbeses, R. C. Clin. Chim. Acta 48:109–111 (1973);

electron-dense compounds (ferritin) Singer, S. J. et al, J. Biophys. Biochem. Cyto; 9: 519–537 (1961); protein–bacteriophage conjugates, (Haimovich, J. et al, Biochim. Biophys. Acta 207:115–124 (1970); or stable free radicals (Bastiani, R. J., et al, Am. J. Med. Technol. 39:211–216 (1973).

Because of the high affinity and specificity of the monoclonal IgM antibodies of the present invention it is also possible to use the same in purification methodologies. The most common of these comprises binding the hybridomal IgM antibody on a cellulose based solid phase support, adding a complex mixture containing the vital antigen recognizable by the antibody, thereby binding said antigen to said antibody, washing the column extensively with buffers and eluting the viral antigen by changing the column conditions, such as the ionic strength, the pH or the like.

Having now generally described this invention, the same will be better understood by reference to certain specific examples which are included herein for purposes of illustration only and are not intended to be limiting of the invention or any embodiment thereof, unless specified.

EXAMPLE 1

This example describes the use of IgM monoclonal antibodies to hepatitis B surface antigen (HBsAg) in several solid phase radioimmunoassays. Two general types of radioimmunoassays are defined. One assay is performed in the reverse direction. Under these experimental conditions serum containing the hepatitis antigen is first incubated with $^{125}$I-monoclonal IgG or IgM antihepatitis B antigen, or heterologous antihepatitis B (prepared by conventional immunizations) followed by a second incubation with monoclonal IgM anti HBs or heterologous anti-HBs coupled to a solid phase, for example polystyrene beads. The other assay is performed in the forward direction. In this protocol, monoclonal IgM anti-HBs or heterologous anti-HBs coupled to a solid phase is first incubated with serum containing HBsAg. The second incubation, therefore, is comprised of $^{125}$I-monoclonal IgG or IgM anti-HBs or heterologous anti-HBs. The sensitivity and specificity of the monoclonal IgM and IgG anti-HBs sandwich assays are compared directly to conventional assays either alone or in combination with anti-HBs prepared by standard animal immunizations.

MATERIALS AND METHODS

Monoclonal IgM and IgG antibodies with specificity for HBsAg were obtained according to the procedures described by Wands and Zurawski copending U.S. patent application Ser. No. 086,947, Oct. 22, 1979 now U.S. Pat. No. 4,271,145. One quarter inch plastic beads were obtained commercially; identical beads coated with conventionally prepared antibodies to HBsAg (AUSRIA II) were also obtained commercially (Abbott Laboratories, N. Chicago, Ill.)

Plastic beads were coated with IgM hybridomal anti-HBs as follows: Ascites fluid derived from malignant growth in BALB/mice of double cloned hybridoma cell lines which produce IgM anti-HBs antibodies was diluted 1:1000 to 1:5000 in phosphate buffered saline. The beads were incubated for 16 hours at room temperature and washed X3 with distilled water: the beads coated with IgM anti-HBs were then ready for use in the RIAs. The HBsAg was radiolabeled with Na$^{125}$I using the chloramine T method of Hunter and Greenwood, Nature 194:495 (1962) or Hunter and Bolton, Biochemical Journal, 133: 529-(1973); specific activity ranged from 0.1 to 0.4 $\mu$Ci/$\mu$g and incorporation of $^{125}$I was 20–26 percent. The monoclonal IgG anti-HBs antibodies were also labeled according to the above method; specific activity ranged from 0.1 to 15 $\mu$Ci/$\mu$g and incorporation of radio-label varied from 20 to 50 percent.

Assays were carried out with various combinations of coated beads and labeled antibodies or antigen to establish the efficacy of the technology. In general individual coated beads were washed X3 with distilled water then mixed with dilutions of patient sera, HBsAg standards, radiolabeled HBsAg or anti-HBs as described in the results. Following washing, the beads were reincubated with radiolabeled reagents as necessary, washed, collected and counted in a Packard gamma well spectrometer. Incubation time varied between 1 and 16 hours as described below.

RESULTS

Table 1 represents the kinetic binding data obtained when plastic beads coated with monoclonal IgM anti-HBs (designated 5D3 and 1F8) were incubated with labeled $^{125}$I-HBsAg.

TABLE I

Comparison of $^{125}$I-HBsAg binding between monoclonal IgM anti-HBs coated beads and beads coated with conventionally prepared guinea pig anti-HBs (AUSRIA II)

| Time (hrs) | AUSRIA II | %** | 5D3+ | cpm bound* % | 1F8‡ | % |
|---|---|---|---|---|---|---|
| 1 | 20,286 ± 412 | 8.1 | 15,261 ± 106 | 12.0 | 13,216 ± 940 | 10.4 |
| 2 | 15,731 ± 621 | 12.4 | 22,916 ± 310 | 18.2 | 19,419 ± 612 | 15.4 |
| 3 | 22,216 ± 491 | 17.6 | 31,916 ± 290 | 25.3 | 29,312 ± 416 | 23.3 |
| 4 | 26,219 ± 301 | 20.8 | 45,000 ± 216 | 35.7 | 42,101 ± 601 | 33.4 |
| 7 | 35,109 ± 720 | 27.8 | 55,109 ± 690 | 43.7 | 54,469 ± 888 | 43.2 |
| 12 | 42,509 ± 612 | 33.7 | 62,916 ± 94 | 49.9 | 60,001 ± 714 | 47.6 |
| 16 | 48,216 ± 819 | 38.2 | 75,928 ± 110 | 60.3 | — | — |
| 24 | 57,016 ± 126 | 45.2 | 89,912 ± 430 | 70.5 | — | — |

*126,000 cpm $^{125}$I-HBsAg added to coated beads
**Percent of total cpm bound
+5D3 is a monoclonal IgM anti-HBs with specificity for adw and ayw subtypes
‡ 1F8 is a monoclonal antibody with specificity primarily to adw subtype It is evident that the two monoclonal IgM coated beads bind HBsAg at a faster rate than the conventional AUSRIA II IgG anti-HBs antibodies. Moreover, a greater percent of total $^{125}$I-HBsAg added is bound at 24 hours by the IgM antibodies. A simple substitution was made of the 5D3 coated beads for the AUSRIA II coated beads and the sensitivity of the two assays was directly compared as shown in Table II. In this experiment dilutions of 2 patients' sera known to contain HBsAg were incubated with 5D3 coated beads or AUSRIA II beads for 16 hours. The beads were washed X3 with distilled water. 200 μl (150,000 cpm) of AUSRIA II $^{125}$I-guinea pig antibodies (anti-HBs) prepared by conventional immunization were then added to both sets of beads for 4 hours. The beads were washed again and counted.

Improvement in the AUSRIA II radioimmunoassay for measurement of HBsAg in serum substitution of monoclonal IgM anti-HBs coated beads for the AUSRIA II beads

| Patient | Serum dilution | Mean cpm* AUSRIA II | Mean cpm** 5D3 | S/N+ AUSRIA II | S/N+ 5D3 |
|---|---|---|---|---|---|
| 1 | 1 × 10⁴ | 5,666 | 16,308 | 35 | 130 |
|   | 1 × 10⁵ | 2,849 | 4,289 | 18 | 34 |
|   | 2 × 10⁵ | 2,145 | 3,084 | 13 | 27 |
|   | 4 × 10⁵ | 1,249 | 1,857 | 7.7 | 15 |
|   | 8 × 10⁵ | 819 | 1,144 | 5.5 | 9.1 |
|   | 16 × 10⁵ | 512 | 615 | 3.5 | 6.0 |
| 2 | 1 × 10⁴ | 6,061 | 14,883 | 38 | 119 |
|   | 1 × 10⁵ | 2,652 | 4,486 | 16 | 36 |
|   | 2 × 10⁵ | 1,810 | 2,388 | 11.2 | 19 |
|   | 4 × 10⁵ | 1,249 | 1,679 | 7.8 | 13 |
|   | 8 × 10⁵ | 774 | 893 | 4.8 | 8 |
|   | 16 × 10⁵ | 625 | 545 | 3.9 | 5 |
| Negative Controls | — | 161 | 125 | | |

*AUSRIA II beads incubated × 16 hr with 200 μl of patients serum, washed 3× with distilled water followed by a 4 hour incubation with $^{125}$I-anti-HBs conventionally prepared in guinea pig and washed ×3 in distilled water. Beads counted in gamma counter.
**Procedure and reagents identical to above except 5D3 coated beads substituted for AUSRIA II beads.
+S/N is the signal/noise calculated by dividing the mean cpm in test sample by mean cpm of the negative controls.

It is evident from Table II that a simple substitution of the 5D3 coated beads improved the AUSRIA II assay at both high and low HBsAg concentrations. Furthermore, the background counts exhibited by the negative control sera was lowered by beads; thus the specificity of the RIA was also substituting the 5D3 IgM coated beads for AUSRIA II improved. That is, not only did the assay detect more antigen as shown-by the cpm bound but the signal to noise ratio was also enhanced (calculated by dividing the cpm bound by background cpm of the negative control); the experimental data indicates that the sensitivity of the assay has been increased as well.

A reverse sandwich assay using 1) a total monoclonal system or 2) a combination of IgM and IgG monoclonal anti-HBs antibodies with the AUSRIA II reagents was then prepared. The incubation conditions were identical for all assays and therefore, the results are directly comparable.

A HBsAg standard was first incubated at 10 ng/ml with $^{125}$I-anti-HBs (guinea pig antisera AUSRIA II) or monoclonal IgG $^{125}$I-anti-HBs of varying specific activities (0.1 to 16 μCi/μg) for 1 hour at 45° C. Beads were washed and counted. The results are depicted in Table III.

TABLE III

Sensitivity of a 2 hr reverse monoclonal anti-HBs sandwich RIA for HBsAg and improvement of AUSRIA II reagents by substitution with monoclonal anti-HBs antibodies.

| Monoclonal* antibody | cpm** 5D3 beads | cpm neg. cont. | cpm+ AUSRIA II beads | cpm neg. cont. | S/N 5D3 | S/N AUSRIA II |
|---|---|---|---|---|---|---|
| $^{125}$I-1C7-PA | 20,809 | 235 | 20,632 | 136 | 88.5 | 151.7 |
| $^{125}$I-1C7-J | 5,138 | 50 | 5,672 | 40 | 113.4 | 141.8 |
| $^{125}$I-1C7-C | 19,131 | 214 | 16,697 | 321 | 89.4 | 52.0 |
| $^{125}$I-4E8 | 15,619 | 196 | 14,916 | 340 | 79.7 | 43.8 |
| $^{125}$I-anti-HBs (AUSRIA II) | 3,634 | 26 | 1,987 | 21 | 139.8 | 94.0‡ |

*1C7-PA, 1C7-J, and 1C7-C are IgG, monoclonal anti-HBs antibodies labeled with different specific activities. These antibodies were incubated with 10 ng/ml of HBsAg standard for 1 hr at 45° C.
**5D3, an IgM monoclonal anti-HBs, was coated to beads and incubated for a second 1 hr period. Washed ×3 and counted.
+AUSRIA II beads added as the second component instead of 5D3 coated beads.
‡ AUSRIA II run in the forward direction (e.g. beads first incubated for 1 hr at 45° C. with HBs Ag standard, then washed, and 200 μl $^{125}$I-anti-HBs (guinea pig) added for an additional 1 hr period) yields a S/N of 20.6.

It is noteworthy that the sensitivity of the RIAs has been improved under all experimental conditions: further the total monoclonal sandwich assay was very sensitive for detection of HBsAg. In addition, the AUSRIA II assay was also substantially improved by the use of $^{125}$I-IgG monoclonal anti-HBs or by substituting the 5D3 coated beads for their beads in the reverse direction assay. These studies establish the value of monoclonal anti-HBs antibodies as a sensitive and specific probe either alone or in combination with the AUSRIA II or the like reagents in the improvement of immunoassays for HBsAg.

Investigations were performed to determine the sensitivity by a quantitative titration of HBsAg standards as shown in Table IV.

TABLE IV

Development of a more sensitive 2 hour reverse sandwich monoclonal RIA for HBsAg with a quantitative comparison to the AUSRIA II RIA

| Dilution | Conc. HBsAg ng/ml | Mean cpm* AUSRIA II | Mean cpm** 5D3 + 1C7 | S/N+ AUSRIA II | S/N 5D3 + 1C7 |
|---|---|---|---|---|---|
| Undiluted | 20 | 4,864 | 19,992 | 94.8 | 995.5 |
| 1:2 | 10 | 2,098 | 608 | 27.9 | 30.0 |
| 1:4 | 5 | 972 | 397 | 14.9 | 20.0 |
| 1:8 | 2.5 | 560 | 180 | 8.60 | 9.0 |
| 1:16 | 1.25 | 279 | 164 | 4.41 | 8.2 |
| 1:32 | .625 | 62 | 98 | .95 | 4.9 |
| 1:64 | .312 | 81 | 42 | 1.2 | 2.0 |
| Neg. controls | | 65 | 20 | | |

*Assay performed by incubating AUSRIA II beads ×1 hour at 45° C. with 200 μl of HBsAg standards. Beads were washed ×3 followed by the addition of 200 μl $^{125}$I-anti-HBS (AUSRIA II: 166,642 cpm) for an additional 1 hr period. Beads washed and counted in a gamma counter.
**Assay performed in the reverse direction where antigen standard (200 μl) added to 1C7 $^{125}$I-IgG₁ monoclonal anti-HBs (150,000 cpm) for 1 hour at 45% C.. Then 5D3 coated beads were added for an additional 1 hour period. Beads were washed and counted as above.
+S/N represents signal to noise ratio by dividing mean cpm of test sample by mean cpm of control. Note that the total monoclonal reverse sandwich assay detected HBsAg at a concentration of 0.301 ng/ml.

In this experiment a total monoclonal assay was compared with AUSRIA II; both assays were run in the reverse direction as described above. AUSRIA II detected HBsAg at a level of 1.25 ng/ml in the reverse direction as described above. AUSRIA II detected HBsAg at a level of 1.25 ng/ml in the reverse direction (lowest level of sensitivity was 2.5 ng/ml in the forward direction.). A combination of 5D3 coated beads with monoclonal $^{125}$I-IgG anti-HBs (1C7), however detected HBsAg at 0.3012 ng/ml which represent an approximate 4-fold increase in sensitivity. The data suggest again that a monoclonal IgM and IgG system was superior to conventional assays.

An assay run was developed in the forward direction either alone or in combination with AUSRIA II reagents. Table V illustrates the results of these experiments.

TABLE V

Development of a monoclonal assay for HBsAg in the forward direction with comparison to the AUSRIA II reagents.

| Serum dilution | Mean* cpm 5D3 + 1 C7 | Mean** cpm AUSRIA II | Mean + cpm AUSRIA II + 1C7 | Mean‡ cpm 5D3 + AUSRIA II |
|---|---|---|---|---|
| Undiluted | 9,260 | 8,924 | 10,117 | 6,184 |
| 1 × 10$^1$ | 6,251 | 4,621 | 9,162 | 3,215 |
| 1 × 10$^2$ | 3,418 | 1,151 | 7,164 | 2,001 |
| 1 × 10$^3$ | 2,969 | 962 | 6,218 | 943 |
| 1 × 10$^4$ | 2,169 | 213 | 5,164 | 512 |
| Neg. controls | 992 | 150 | 1,521 | 150 |

*Serum dilutions incubated for 16 hrs with 5D3 coated beads. Beads washed ×3 with distilled water. The second incubation was for 4 hrs with $^{125}$I-1C7 (160,000 cpm). Beads were washed and counted.
**Standard AUSRIA II radioimmunoassay performed in an identical manner to that mentioned above.
+Identical radioimmunoassay but where $^{125}$I-1C7 was substituted for $^{125}$I-anti-HBs (AUSRIA II)
‡Identical radioimmunoassay but where $^{125}$I-anti-HBs (AUSRIA II) was substituted for $^{125}$I-1C7 and AUSRIA II beads were substituted for 5D3 coated beads.

All assays were performed under the following conditions: HBsAg positive dilutions (200 μl) were incubated with 5D3 or AUSRIA II beads for 16 hours at room temperature. The beads were washed X3 with distilled water. The second incubation covered 4 hours at room temperature with either monoclonal $^{125}$I-anti-HBs (AUSRIA II) probes. Tables V and VI demonstrate that very sensitive RIA's performed in the forward and reverse directions were developed using either a total monoclonal IgG-IgM or IgM-IgM system or a combination assay of monoclonal antibodies with AUSRIA II reagents.

TABLE VI

Development of a total IgM monoclonal anti HBs reverse sandwich assay demonstrating enhanced sensitivity compared to AUSRIA II

| Dilution HBsAg Standard | Conc. HBsAg (ng/ml) | cpm* bound 5D3 + 5D3 | S/N | cpm** bound AUSRIA II | S/N |
|---|---|---|---|---|---|
| 1:2 | 10 | 1010 | 6.97 | 3398 | 26.14 |
| 1:4 | 5 | 1449 | 9.99 | 793 | 6.10 |
| 1:8 | 2.5 | 1457 | 10.04 | 404 | 3.10 |
| 1:16 | 1.25 | 1713 | 11.82 | 256 | 1.96 |
| 1:32 | 0.625 | 1800 | 12.42 | 183 | 1.40 |
| 1:64 | 0.312 | 1749 | 12.06 | 205 | 1.57 |
| 1:128 | 0.156 | 1415 | 9.75 | 223 | 1.71 |
| 1:256 | 0.078 | 687 | 4.74 | 176 | 1.35 |
| 1:512 | 0.039 | 116 | 0.80 | 156 | 1.20 |
| Neg. controls | — | 145 | | 130 | |

*$^{125}$I-5D3 (IgM monoclonal anti-HBs) first incubated with HBsAg standards (2000,00 cpm) for 1 hr at 45° C., then 5D3 coated beads were added for a further 1 hr incubation at 45° C.. Beads were washed ×3 with distilled water and counted.
**Standard AUSRIA RIA run in the forward direction under the same incubation conditions as mentioned above.

EXAMPLE II

This example describes the use of monoclonal IgM anti-HBs in the biopurification of HBsAg from serum.

MATERIALS AND METHODS

Monoclonal IgM anti-HBs affinity columns were prepared by coupling 28 and 65 mg of ascites fluid protein derived from cell lines 5D3 and 2F11 respectively to cyanogen bromide activated Sepharose 6B; Williams et al, Cell 12:663 (1977). One control column was comprised of cyanogen bromide activated Sepharose 6B alone and the other was coupled to 30 mg of mouse serum. Human serum (10 mg) derived from a high titer chronic HBsAg (adw subtype) carrier patient was placed over all four columns and incubated for 24 hours at room temperature. The columns were extensively washed with PBS. Subsequently, 1 ml fractions were collected by elution with glycine-HCl buffer pH 2.6. The pH of each fraction was adjusted to 7.4 with 0.1N NaOH and the protein concentration, Lowry et al, J. Biol. Chem. 193:265 (1951) and HBsAg activity (AUSRIA II), was determined.

RESULTS

Figure 1:
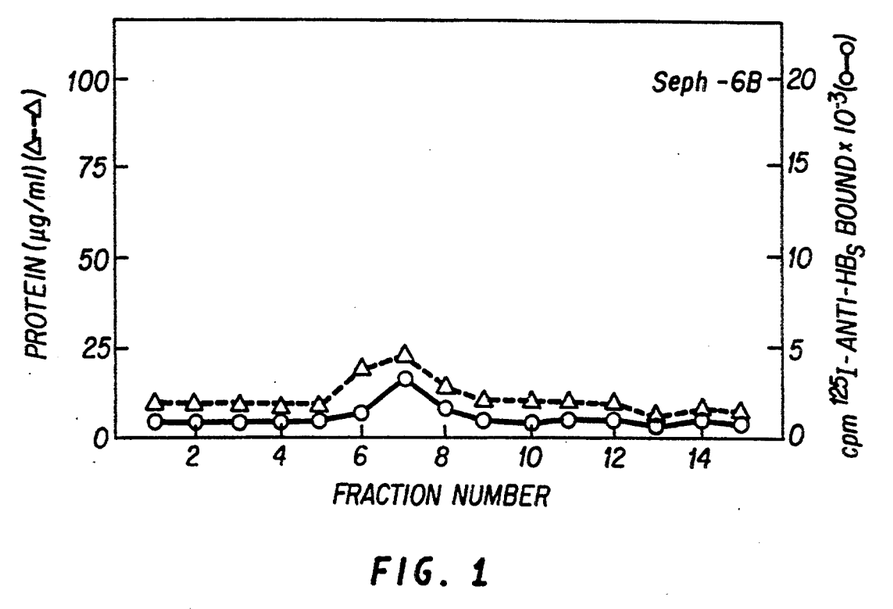
FIG. 1 shows the purification of hepatitis B surface antigen (HBsAg) of the adw subtype from serum, with a hybridomally produced monoclonal IgM anti-HBs affinity column. The elution profile of protein and HBsAg activity is measured by a solid phase radioimmunoassay from a cyanogen bromide activated Sepharose 6B control column.
Figure 2:
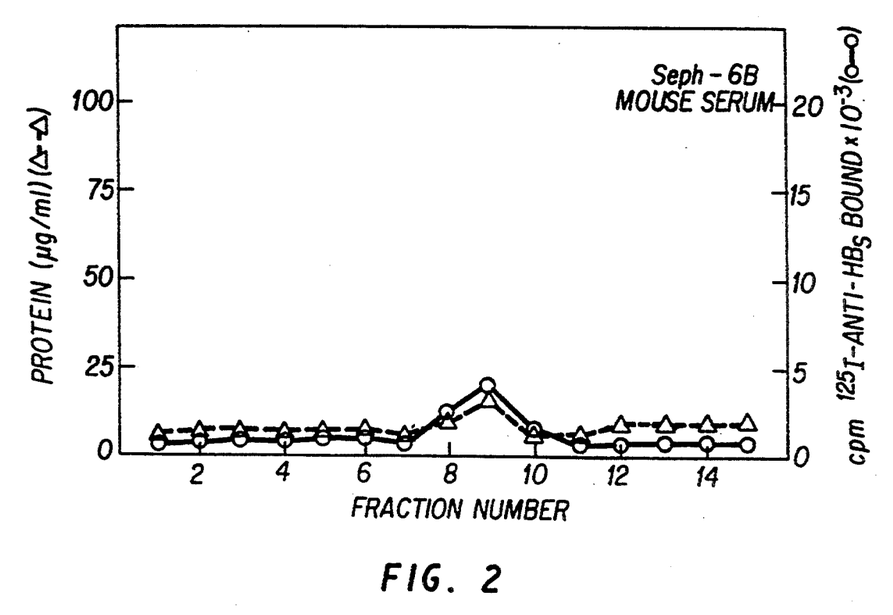
FIG. 2 shows a similar purification to that of FIG. 1 wherein the elution profile is from a control column prepared with 30 mg of mouse serum.
Figure 3:
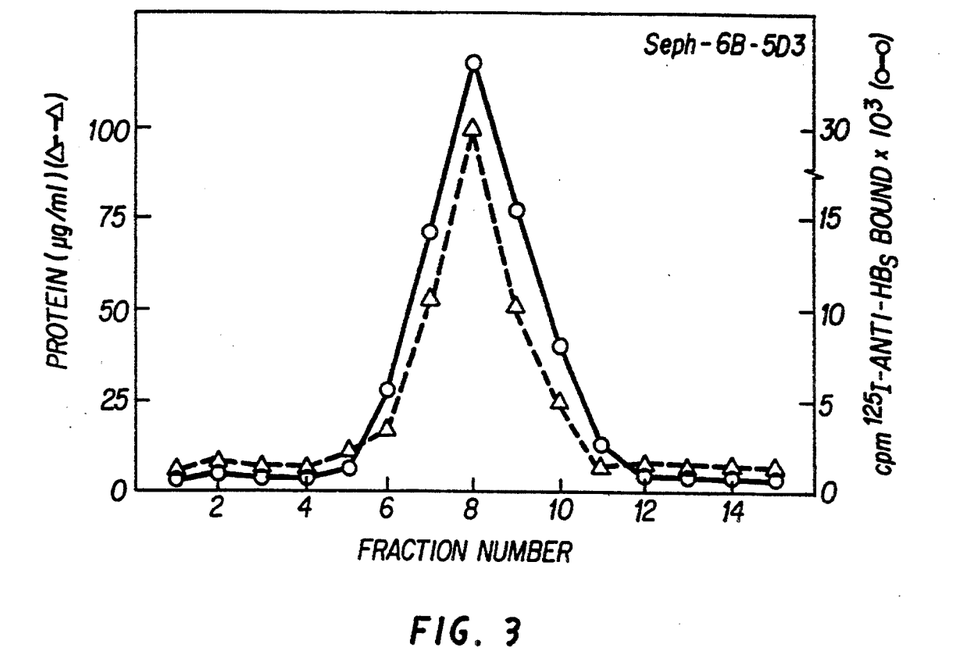
Figure 4:
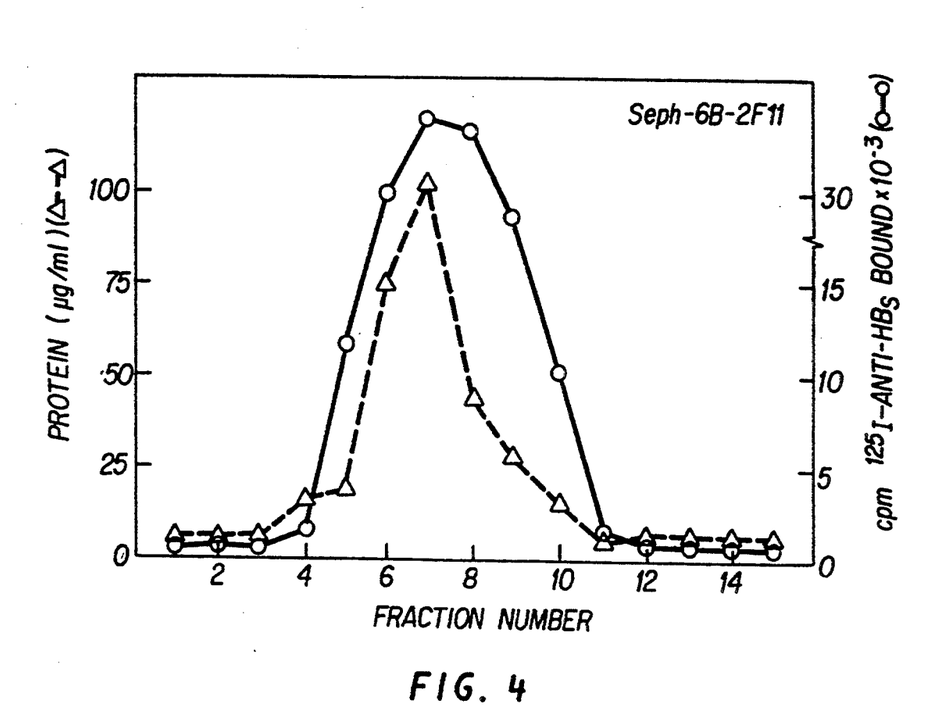

FIGS. 1–4 demonstrate that HBsAg (adw subtype) present in serum, bound to the monoclonal IgM anti-HBs affinity columns prepared from ascites fluid derived from clones 5D3 (FIG. 3) and 2F11 (FIG. 4). It is noteworthy that previous studies have established that monoclonal IgM anti-HBs from 2F11 and 5D3 recognized the adw subtype. Subsequently, the HBsAg could be recovered from the columns in μg amounts by elution with glycine HCl buffer pH 2.6. In contrast, there was no significant binding of HBsAg to the Sepharose 6B column (FIG. 1) or to Sepharose 6B coupled to mouse serum (FIG. 2). This study illustrates the use of monoclonal IgM in the purification and characterization of antigens.

EXAMPLE III

This example describes the use of monoclonal IgM antibodies in the detection of HBsAg coated to red blood cells. The experiments demonstrate that is also feasible to detect free HBsAg in serum by first coating IgM anti-HBS to red blood cells and incubating such cells with HBsAg-containing serum to produce a hemagglutination reaction.

MATERIALS AND METHODS

Human O-negative red blood cells coated with HBsAg subtypes adw and ayw were purchased commercially. 25 μl of buffer was placed in microtiter plates followed by serial 2-fold dilution of culture supernatants and ascites fluid from three IgM anti-HBs producing hybridoma cell lines: plates were incubated at 37° C. for 30 minutes. Following this incubation 25 μl of a 0.1% solution of HBsAg coated cells were added to each well. The reaction mixture was allowed to incubate at 37° C. for 30 minutes, plates were centrifuged at 300×g for 2 minutes and placed at a 45° angle. After 10 minutes the plates were assessed for the presence or absence of hemagglutination.

RESULTS

Studies were performed with HBsAg coated human O-negative red blood cells in order to determine if the monoclonal IgM anti-HBs antibodies possessed agglutinating properties and recognized subtypes of HBsAg as shown in Table VII.

TABLE VII

Hemagglutination titer of IgM anti-HBs for HBsAg (adw and ayw) coated human red blood cells

| Cell line | Culture supernatants* | | Ascites fluid* | |
|---|---|---|---|---|
| | ayw | adw | ayw | adw |
| 1F8 | 1:4 | 1:2.6 × 10$^5$ | 1:2.6 × 10$^4$ | 1:1.7 × 10$^{10}$ |
| 2F11 | 1.4 | 1:1.3 × 10$^5$ | 1:1 0 × 10$^6$ | 1:1.3 × 10$^{11}$ |
| 5D3 | 1:2.1 × 10$^9$ | 1:3.2 × 10$^7$ | 1:2.2 × 10$^{12}$ | 1:2.7 × 10$^{11}$ |
| Con- | <1:4 | <1:4 | <1:4 | <1:4 |

TABLE VII-continued trols‡

*Hemagglutination titer of HBsAg coated human O negative red blood cells HBsAg subtypes adw and ayw). Positive titers are considered 1:4 or greater. Data are expressed as the final dilutions of the original 25 μl of ascites fluid and cell culture supernatants which gave a hemagglutination reaction.
‡Controls consist of ascites fluid containing IgG₁ monoclonal antibodies to cardiac myosin, reacting with HBsAg coated cells. Ascites fluid from the above three cloned cell lines reacting with human O negative red blood cells (HBsAg negative) and mouse myeloma IgM 1 mg/ml in phosphate buffered saline reacting with HBsAg coated red blood cells and control red blood cells.

It is of great interest that these IgM anti-HBs are exceptionally good agglutinating antibodies. For example 25 μl of cell supernatant from line 5D3 gave hemagglutination titers of $1:2.1 \times 10^9$ and $1:3.2 \times 10^7$ for HBsAg (ayw and adw) coated red blood cells respectively. Further, the agglutinating capacity was amplified in the ascites fluid since extraordinary high titers of $1:2.2 \times 10^{12}$ and $1:2.7 \times 10^{11}$ were noted for the same HBsAg coated cells. Indeed it is remarkable that 25 μl of ascites fluid diluted at $1:2.2 \times 10^{12}$ still gave a positive agglutination reaction and illustrates the apparent high avidity of this IgM anti-HBs for HBsAg coupled indicator cells. Thus, the above data indicates that monoclonal IgM anti-HBs is an extremely potent antibody for hemagglutination reactions, and is of considerable use in the detection of HBsAg in serum by first coating the antibody to red blood cells and reacting such cells with HBsAg positive serum.

EXAMPLE IV

In this example, it is demonstrated that monoclonal IgM anti-HBs may be employed as a probe for detection of anti-HBs in serum by an inhibition radioimmunoassay.

MATERIALS AND METHODS

In this assay μl of human serum containing anti-HBsAg (5 ng/ml) followed by the addition of monoclonal $^{125}$I-1C7 (200,000 cpm) and incubated for 1 hour at 45° C. The beads were washed ×3 with distilled water and counted in a gamma well counter.

RESULTS

Table VIII illustrates the results of the experiment.

TABLE VIII

Development of a monoclonal radioimmunoassay for anti-HBs in serum by inhibitor of antigen (HBsAg) binding

| Serum dilution* | mean cpm** bound |
|---|---|
| Undiluted | 106 |
| $1 \times 10^1$ | 131 |
| $1 \times 10^2$ | 492 |
| $1 \times 10^3$ | 1,062 |
| $1 \times 10^4$ | 2,615 |
| Neg controls X | 98 |

*Patient serum containing anti-HBs.
**The assay was performed as follows: serum containing anti-HBs (bound 15,612 cpm in AUSAB radioimmunoassay) was added to a fixed concentration of unlabeled HBsAg followed by the addition of $^{125}$I-1C7 (monoclonal IgG₁ anti-HBS) and incubated for 1 hr. at 45° C.. Next 5D3 coated beads (IgM monoclonal anti-HBs) were added to the reaction mixture for 1 hr., washed ×3 and counted in a Packard gamma counter. Antibody to hepatitis B surface antigen (anti-HBs) in serum complexed with added HBsAg and therefore was unavailable for binding with $^{125}$I-1C7 monoclonal anti-HBs at undiluted and a 1:10 serum dilution. However, as the concentration of anti-HBs becomes lower as the result of further dilution, the HBsAg now becomes available for binding to $^{125}$I-1C7 anti-HBs. Thus, free HBsAg was now in excess of anti-HBs in serum and was detectable in the RIA with increasing serum dilution. This assay, therefore, measures inhibition of antigen binding by serum containing anti-HBs and is a sensitive method for detection of such antibodies.

The number of counts of $^{125}$I-1C7 (monoclonal IgG₁ anti-HBs) bound to the beads increased with progressive serum dilution. This binding results from the fact that antibody to hepatitis B surface antigen (anti-HBs) in test serum complexes first to HBsAg, and therefore was unavailable for binding with the radiolabeled probe ($^{125}$I-1C7) at both the undiluted and 1:10 serum dilution. However, as the concentration of anti-HBs in serum becomes lower as the result of further dilution, the added HBsAg (5 ng/ml) now becomes available for binding to $^{125}$I-1C7 anti-HBs. Thus, HBsAg is now in excess of anti-HBs concentrations in serum at the higher dilutions and is detectable as shown by increasing cpm bound to the 5D3 coated beads in the RIA. This assay therefore measures inhibition of antigen binding (HBsAg) by serum containing anti-HBs and is a sensitive method for detection of such antibodies.

COMPARATIVE EXAMPLE

The affinity of anti-HBsAg monoclonal IgM for HBsAg was measured by Scatchard analysis and the results are as follows:

| Antibody | $K_d(M^{-1})$ | Ref |
|---|---|---|
| Hybridomally produced IgM of present invention against HBsAg | $0.048 - 4.1 \times 10^{11}$ | invention |

The affinity constants expressed in this table and elsewhere in this application and claims refer to binding affinities per molecule of IgM and should not be construed to represent affinities per binding site of IgM.

Cell line 5D3, producing the monoclonal IgM anti-HBs described in the examples, was deposited at the American Type Culture Collection, Rockville, Md., on Aug. 25, 1988, under the Budapest Treaty, and given ATCC Accession No. HB9801.

What is claimed as new and desired to be secured by letters patent of the United States is:

1. In an immunometric assay to determine the presence or concentration of an antigenic substance containing HBsAg determinants in a sample of a fluid comprising forming a ternary complex of a first labelled antibody, said antigenic substance, and a second antibody, said second antibody being bound to a solid carrier insoluble in said fluid, wherein the presence of the antigenic substance in the sample is determined by measuring either the amount of labelled antibody bound to the solid carrier, or the amount of unreacted labelled antibody, the improvement comprising employing IgM monoclonal antibodies which bind to HBsAg determinants per se and having an affinity for the antigenic substance containing HBsAg determinants of at least $10^9$ liters/mole for each of said labelled antibody and said antibody bound to a solid carrier.

2. A process according to claim 1 wherein the fluid sample is first contacted with the second monoclonal antibody to form a binary complex of the antigenic substance and said second monoclonal antibody insoluble in the fluid and then contacted with said first labelled monoclonal antibody to form the ternary complex.

3. A process according to claim 1 wherein the fluid sample is first contacted with the second monoclonal antibody to form a binary complex of the antigenic substance and said second monoclonal antibody insoluble in the fluid; the sample separated from the solid carrier and the solid carrier contacted with a solution of said first labelled monoclonal antibody to form said ternary complex.

4. A process according to claim 3 wherein said solid carrier after formation of the ternary complex is washed to separate the fluid sample from the carrier.

5. A process according to claim 4 wherein the solid carrier is washed with phosphate buffered saline.

6. A process according to claims 1, 2 or 3 wherein the antigenic substance is Hepatitis B virus.

7. A process according to claims 1, 2 or 3 wherein the labelled antibody is labelled with a member selected from the group consisting of a radioactive isotope, an enzyme and a fluorogenic material.

8. A process according to claim 7 wherein said label is the radioactive isotope $^{125}I$.

* * * * *